United States Patent
Brandt et al.

(10) Patent No.: US 11,207,259 B2
(45) Date of Patent: Dec. 28, 2021

(54) COSMETIC PRODUCTS FOR THE TEMPORARY RESHAPING OF KERATINOUS FIBERS WITH LONG-LASTING HOLD

(71) Applicant: Henkel AG & Co. KGaA, Duesseldorf (DE)

(72) Inventors: Sandra Brandt, Pinneberg (DE); Marcus Noll, Quickborn (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 16/220,913

(22) Filed: Dec. 14, 2018

(65) Prior Publication Data
US 2019/0183772 A1  Jun. 20, 2019

(30) Foreign Application Priority Data
Dec. 15, 2017 (DE) ............ 10 2017 222 857.1

(51) Int. Cl.
*A61K 8/73* (2006.01)
*A61Q 5/06* (2006.01)
*A61K 8/04* (2006.01)

(52) U.S. Cl.
CPC ............ *A61K 8/732* (2013.01); *A61K 8/042* (2013.01); *A61K 8/73* (2013.01); *A61Q 5/06* (2013.01); *A61K 2800/48* (2013.01)

(58) Field of Classification Search
CPC .... A61K 8/732; A61K 8/042; A61K 2800/48; A61Q 5/06
See application file for complete search history.

(56) References Cited

U.S. PATENT DOCUMENTS

2008/0131469 A1* 6/2008 Hashimoto .......... A61K 8/0208
424/401
2013/0022565 A1 1/2013 Braida-ValeRio et al.
2016/0317396 A1* 11/2016 Perfitt .................. A61K 8/26

FOREIGN PATENT DOCUMENTS

| FR | 2892625 A1 | 5/2007 |
| FR | 2958155 A1 | 10/2011 |
| GB | 2536305 A | 9/2016 |
| WO | 2012084759 A2 | 6/2012 |
| WO | WO-2017080625 A1 * | 5/2017 ........... A61K 9/1623 |

OTHER PUBLICATIONS

Beewax, Chemicalbook, ([retrieved from on-line website: https://www.chemicalbook.com/ChemicalProductProperty_EN_CB6684200.htm, last visit date Oct. 23, 2020]) (Year: 2020).*

* cited by examiner

*Primary Examiner* — Kyung S Chang
(74) *Attorney, Agent, or Firm* — Lorenz & Kopf, LLP

(57) ABSTRACT

The present disclosure relates to a cosmetic product for the temporary reshaping of keratinous fibers, particularly human hair, containing potato starch and dehydroxanthan gum.

10 Claims, No Drawings

COSMETIC PRODUCTS FOR THE TEMPORARY RESHAPING OF KERATINOUS FIBERS WITH LONG-LASTING HOLD

CROSS-REFERENCE TO RELATED APPLICATION

This application claims priority to German Patent Application No. 10 2017 222 857.1, filed Dec. 15, 2017, which is incorporated herein by reference in its entirety.

TECHNICAL FIELD

The present disclosure relates to a cosmetic product for the temporary reshaping of keratinous fibers, particularly human hair.

BACKGROUND

The temporary shaping of hairstyles for a prolonged period of up to several days typically requires the use of stabilizing agents. This is why hair treatment products that serve to hold the hair temporarily play an important part. Corresponding substances for temporary reshaping usually contain synthetic polymers and/or waxes as the stabilizing substance. Products for supporting the temporary reshaping of hair may be manufactured in the form of hairspray, hair wax, hair gel or hair mousse, for example.

An important property of a product for the temporary reshaping of hair, also called styling product in the following text, includes providing the treated fibers with a hold that lasts as long as possible in the newly modeled shape—that is to say a shape that has been imposed on the hair. This is referred to as a long hairstyle hold or a long-lasting hold strength of the styling product. The hairstyle hold is determined mainly by the nature and quantity of the stabilizing agent, although the other components of the styling product may also have some effect.

Besides a long-lasting hold strength, styling products must also satisfy a whole range of other requirements. These can be defined roughly as properties on the hair, properties of the respective formulation, for example the properties of the foam, gel or sprayed aerosol, and properties relating to the handling of the styling product, wherein the properties on the hair are particularly important. These especially include moisture resistance, low tack and a balanced conditioning effect. In addition, a styling product should also be usable for as many hair types as possible, and it should be gentle on the hair and skin.

In order to satisfy the various requirements, many synthetic polymers have already been developed as stabilizing agents and are used in styling products. The polymers can be divided into cationic, anionic, non-ionic and amphoteric stabilizing polymers. Waxes may be used as alternative or additional stabilizing agents. Ideally, when used on the hair the polymers and/or waxes form a polymer film or film, which on the one hand lends the hairstyle a long-lasting hold of the desired strength, but at the same time is also flexible enough not to break under strain.

BRIEF SUMMARY

Cosmetic products and methods for temporarily reshaping keratinous fibers are provided. In an exemplary embodiment, a cosmetic product comprises water, potato starch, and dehydroxanthan gum. The water is present at from about 1 to about 97 weight percent, based on a total weight of the cosmetic product, and the potato starch is present at from about 0.5 to about 20 weight percent, also based on the total weight of the cosmetic product. The dehydroxanthan gum is present at from about 0.5 to about 3 weight percent, based on the total weight of the cosmetic product.

A method of temporarily reshaping keratinous fibers is provided in another embodiment. The method includes applying a cosmetic product to the keratinous fibers. The cosmetic product comprises water at from about 1 to about 97 weight percent, potato starch at from about 0.5 to about 20 weight percent, and dehydroxanthan gum at from about 0.5 to about 3 weight percent, all based on a total weight of the cosmetic product.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

One object of the present disclosure was to provide further suitable polymers or polymer combinations which are exemplified by good film-forming and/or stabilizing properties and lend hairstyles a long-lasting hold strength.

This object is solved with a cosmetic product for the temporary reshaping of keratinous fibers which contains
from about 1 to about 97% w/w water,
from about 0.5 to about 10% w/w potato starch and
from about 0.5 to about 3% w/w dehydroxanthan gum,
relative in each case to the total weight of the product.

The use of dehydroxanthan gum alone in the cosmetic products thus already lends the treated keratinous fibers a long-lasting hold strength. The stabilizing properties of potato starch are not particularly distinctive in and of themselves. However, in this regard the combination of potato starch and dehydroxanthan gum has a superadditive (synergistic) effect in terms of the long-lasting hold strength which is much stronger than in comparable products on the market. Moreover, dehydroxanthan gum and potato starch are natural, renewable raw materials and are biodegradable. They are thus not associated with the problems of microplastic residue, as are synthetic film-forming agents such as polyvinylpyrrolidone or vinyl pyrrolidone/vinyl acetate copolymers.

Cosmetic products for temporary reshaping of human hair are also called styling products. The present disclosure relates particularly to styling products such as hair gels, hair waxes, pastes, lotions, emulsions or clays. The product form "clay" is used to refer to highly viscous, wax-like cosmetic products which contain among other things clay compounds such as kaolin.

In the course of the present disclosure, it was found surprisingly that an unexpectedly long hold time for hairstyles may be achieved by adding potato starch and dehydroxanthan gum to a cosmetic product for the temporary reshaping of keratinous fibers, particularly human hair. In other words, the length of hold of a hairstyle that is created using a product for temporary reshaping may be prolonged.

Surprisingly, it was found that, contrary to expectations, no negative aspects such as plaque formation were encountered. If the polymer film is too brittle, "film plaque" is formed, that is to say residues which become separated when the hair moves and create the impression that the user of the styling product in question has dandruff.

Other usually required properties of cosmetic products for the temporary reshaping of keratinous fibers, such as low tack, are also retained.

As contemplated herein, the term keratinous fibers extends to fur, wool and feathers, but particularly human hair.

The cosmetic product is preferably a hair gel. For the purposes of the present disclosure, hair gel comprises a water-based or water/alcohol-based hairstyle stabilizer in gel form which is used to create the hairstyle (styling).

Particularly preferred is a cosmetic product in which water makes up from about 30 to about 95% w/w of the total weight of the product.

Similarly, a cosmetic product is preferred which contains a quantity of potato starch (Solanum Tuberosum starch) equal to from about 1 to about 3% w/w relative to the total weight of the product.

In a further embodiment of the present disclosure, a potato starch is used which is partially or completely modified.

Modified starches are starch products that are obtained by physical, enzymatic or chemical processes which satisfy more stringent technical requirements. The grain structure and other essential properties are retained after modification.

The basic material for the production of modified potato starch is natural or degraded starch, which is converted into the respective derivatives by polymer-analog reactions. According to Wikipedia (keyword "Modifizierte Starch" [English entry entitled "Modified starch"], retrieved on Dec. 5, 2017) natural starch is subjected to various chemical transformation processes depending on which properties are to be changed. In the case of some modified starches, several transformation processes are carried out consecutively (for example acetylated oxidized starch):

- Acid-treated starch by reaction with acids (for example with hydrochloric acid, phosphoric acid or sulfuric acid)
- Alkaline modified starch by reaction with alkaline solutions (for example with sodium hydroxide or potassium hydroxide)
- Bleached starch by treatment with peracetic acid, hydrogen peroxide, sodium hypochlorite, sodium chlorite, sulfur dioxide, sulfites, potassium permanganate or ammonium persulfate
- Enzymatically modified starch by treatment with amylases
- Oxidized starch by oxidation (for example with sodium hypochlorite)
- Monostarch phosphate by esterification with phosphorous ester groups (for example phosphoric acid, sodium- or potassium phosphate, phosphonic acid or pentasodium triphosphate)
- Distarch phosphate by esterification with sodium trimetaphosphate or phosphoroxy chloride
- Phosphatized distarch phosphate by combination of the processes for producing monostarch phosphate and distarch phosphate
- Starch acetate or acetylated starch by reaction with acetic acid anhydride or esterification with acetic acid
- Hydroxypropyl starch by reaction with propylene oxide
- Starch sodium octenyl succinate by reaction of starch with octenyl succinic acid anhydride Physically modified starches are equated with the native starches because they are only treated thermally, that is so say they are boiled.

Particularly preferably for the purpose of the present disclosure, before it is used in the product the potato starch is either boiled (gelatinization) or swelled, a process in which an aqueous dispersion of the potato starch is rendered strongly alkaline with NaOH, for example. Then that alkaline solution may be adjusted again to any pH value with an organic acid, lactic acid for example, without interrupting further processing.

A cosmetic product is also particularly preferred in which the quantity of dehydroxanthan gum is from about 1 to about 2% w/w relative to the total weight of the product.

Dehydroxanthan gum (dehydrated xanthan gum with INCI name dehydroxanthan gum) designates a heat-treated xanthan gum which has been exposed to a heat of at least about 40° C. Dehydroxanthan gum has improved dispersibility and is more quickly dispersible in water than xanthan gum which has not undergone heat treatment.

Dehydroxanthan gum is marketed commercially particularly under the name AMAZE® XT (manufactured by Akzo Nobel).

In a preferred embodiment, the dehydroxanthan gum may be formulated with cationic polymers. It may be used with other styling polymers such as acrylate polymers, polyurethane polymers and with PVP and PVP/VA. In one embodiment, the dehydroxanthan gum may be combined with additional thickening agents.

In general, the cosmetic products may additionally contain a natural starch of a different species, particularly wheat starch, tapioca starch, rice starch, corn starch and/or horse chestnut starch. If these starches of other species are contained, it is particularly preferred to use them in quantities from about 10% w/w to about 200% w/w relative to the potato starch.

The cosmetic product may contain a natural or synthetic wax with a melting point higher than about 37° C. as a further component. The cosmetic product may contain the wax in a total quantity from about 1 to about 30% w/w, preferably from about 2 to about 25% w/w and more preferably from about 2.5 to about 20% w/w relative to the total weight of the cosmetic product.

The product preferably contains an emulsifier. In principle, any anionic, cationic, nonionic and ampholytic surface-active compounds which are suitable for application to human skin may be considered for use as emulsifiers. The ampholytic surface-active compounds include zwitterionic surface-active compounds and ampholytes. Nonionic emulsifiers are preferred.

In particular, adducts of ethylene oxide with linear fatty alcohols, fatty acids, fatty acid alkanolamides, fatty acid monoglycerides, sorbitan fatty acid monoesters, fatty acid glycerides, methylglucoside mono fatty acid esters, polydimethyl siloxanes and mixtures thereof are usable as nonionic emulsifiers.

Particularly preferred nonionic surfactants include the adducts of from about 5 to about 60 Mol ethylene oxide with castor oil or hardened (hydrogenated) castor oil. Preferred are ethylene oxide adducts of hardened castor oil, such as are marketed under the name PEG Hydrogenated Castor Oil, for example PEG-30 Hydrogenated Castor Oil, PEG-33 Hydrogenated Castor Oil, PEG-35 Hydrogenated Castor Oil, PEG-36 Hydrogenated Castor Oil or PEG-40 Hydrogenated Castor Oil. Preferred is the use of PEG-40 Hydrogenated Castor Oil.

The cosmetic product may contain the emulsifier in a total quantity of from about 0.1 to about 2% w/w, preferably from about 0.25 to about 1.5% w/w, more preferably still from about 0.5 to about 1% w/w, relative to the total weight of the cosmetic product.

The cosmetic may contain a further component in addition to the potato starch and dehydroxanthan gum to function as a thickener, film-forming agent or gel-forming agent. Examples of such are cationic, anionic, nonionic or amphoteric polymers. The cosmetic product may contain the component functioning as film-forming agent or gel-forming agent in a total quantity from about 1 to about 60% w/w, preferably from about 2 to about 50% w/w, more preferably from about 5 to about 40% w/w, relative to the total weight of the cosmetic product.

However, the present disclosure also extends to embodiments in which the cosmetic product contains no additional components functioning as thickeners, film-forming agent or gel-forming agent other than the potato starch and the dehydroxanthan gum.

Examples of components functioning as thickeners, film-forming agents or gel-forming agents are Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, Ammonium VA/Acrylates Copolymer, AMPD-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, Bacillus/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/Acrylates Copolymer, Octylacrylamide/Acrylates/Butylaminoethyl Methacrylate Copolymer, PEG/PPG-25/25 Dimethicone/Acrylates Copolymer, PEG-8/SMDI Copolymer, Polyacrylamide, Polyacrylate-6, Polybeta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI Copolymer, PPG-10 Sorbitol, PVM/MA Copolymer, PVP, PVPNA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/Isophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VP/VA Copolymer, VP/Vinyl Caprolactam/DMAPA Acrylates Copolymer, Yeast Palmitate or Styrene/VP Copolymer.

Siloxanes are also suitable for use as preferred film-forming polymers. These siloxanes may be either water-soluble or water-insoluble. Both volatile and non-volatile siloxanes are suitable, wherein non-volatile siloxanes are understood to be compounds having a boiling point under normal pressure higher than about 200° C. Preferred siloxanes are polydialkyl siloxanes such as for example polydimethyl siloxane, polyalkylaryl siloxanes such as for example polyphenylmethyl siloxane, ethoxylated polydialkyl siloxanes and polydialkyl siloxanes containing amine and/or hydroxy groups. Glycosidically substituted silicones may also be considered.

Further suitable excipients and additives may particularly include care components such as for example oils, protein hydrolysates, vitamins, provitamins, vitamin precursors.

The cosmetic product may further contain neutralizers or pH adjusting agents in order to adjust the pH. Examples of neutralizers used in cosmetic products are primary aminoalcohols such as aminomethyl propanol (INCI), which is available commercially under the brand name AMP-ULTRA® PC, for example AMP-ULTRA® PC 2000.

The products may further contain cosmetically acceptable preservatives. An example of a preservative which is preferred for use is 2-phenoxyethanol.

The cosmetic product according to the present disclosure may be packaged in forms usual for the temporary reshaping of hair, for example as a wax, paste, lotion, emulsion or clay. The cosmetic products are preferably provided in boxes or pots.

The present disclosure also relates to the cosmetic, non-therapeutic use of the cosmetic products for the temporary reshaping of keratinous fibers, particularly human hair as contemplated herein, use of the cosmetic products for the temporary reshaping of keratinous fibers to lend long-lasting hold to a hairstyle, and a method for temporary reshaping of keratinous fibers, particularly human hair, in which the cosmetic product is applied to keratinous fibers.

Exemplary Embodiment 1

A hair gel was prepared having the following formulation:

| | |
|---|---|
| Water | 96% w/w |
| Potato starch | 2.0% w/w |
| Dehydroxanthan gum[1] | 1.0% w/w |
| Preservative[2] | 1.0% w/w |

Exemplary Embodiment 2

A hair gel was prepared having the following formulation:

| | |
|---|---|
| Water | 94.2% w/w |
| Potato starch | 3.0% w/w |
| Dehydroxanthan gum[1] | 1.0% w/w |
| Preservative[2] | 1.0% w/w |
| Fragrance | 0.3% w/w |
| PEG-40 Hydrogenated Castor Oil | 0.5% w/w |

[1]Amaze ® XT (manufactured by Akzo Nobel Personal Care)
[2]Euxyl PE 9010 (2-phenoxyethanol, ethylhexyl glycerin; (manufactured by Schülke & Mayr)

Comparison Example 1

A formulation was prepared in similar manner to exemplary embodiment 2, but in which dehydroxanthan gum was replaced with the same quantity of carbomer.

Comparison Example 2

A formulation was prepared in similar manner to exemplary embodiment 2, but in which no potato starch but 2.0% w/w dehydroxanthan gum was used.

Comparison Example 3

A formulation was prepared in similar manner to exemplary embodiment 2, but in which besides the dehydroxanthan gum 2.0% w/w Tylose (hydroxyethyl cellulose) was used instead of the potato starch.

The long-term hold of the exemplary embodiment 1 and the comparison examples 1 to 3 was measured.

The compositions were examined with regard to their shaping properties by employing a Long Lasting Hold measurement. For this, standardized strands of hair from the company Kerling (item no. 826500) of the hair type "European Natural, color 6/0" with a length (Lmax) of 220 mm and a weight of 3.0 g were used. To prepare them, the strands were washed with 12.5% w/w solution of sodium laureth sulfate. The hair strands were dried at 45° C. in a drying cabinet overnight.

The hairs were softened in lukewarm water for 20 min and then dabbed until about 50% residual moisture remained in the hairs, 750 mg of the composition to be examined was applied to and massaged into each of the hair strands. The hair strands were placed in a Teflon support, flattened with a steel roller and dried overnight at 21° C. with 80% atmospheric humidity.

The hair strands were then clamped by one end into a holding device and stored for a period of six hours at 21° C. with 85% atmospheric humidity. In order to calculate the Long Lasting Hold (LLH), the lengths of the hair strands protruding from the holding device before (Lo) and after (Lt) storage were measured.

The Long Lasting Hold is a measurement of the change in length over time of a hair strand that has been fixed with a hair reshaping product. The higher the LLH value is, the lower the change in length of the hair strand is under the effects of atmospheric humidity in a certain period of time, and accordingly the better the hold strength of the hair reshaping product is.

The Long Lasting Hold was calculated according to the following formula.

$$LLH = 1 - (Lt - Lo/L \text{ max})$$

For the exemplary embodiment 1, an LLH value of 73% was determined (arithmetical mean from the LLH values of ten test strands). For the comparison example 1, an LLH value of 13% was determined and the gel thus exhibited no long-term hold. For the comparison example 2, an LLH value of 68% and for the comparison example 3, an LLH value of 50% was determined.

The cosmetic product of exemplary embodiment 2 thus exhibited an exceptional long-term hold.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic product for the temporary reshaping of keratinous fibers, consisting of:
   30 to 97% w/w water;
   0.5 to 10% w/w potato starch;
   0.5 to 3% w/w dehydroxanthan gum; and
   at least one care component selected from PEG hydrogenated castor oil, protein hydrolysates, vitamins, provitamins, and vitamin precursors,
   wherein each weight is relative to the total weight of the product.

2. The cosmetic product according to claim 1, wherein the cosmetic product contains no additional components functioning as film-forming agents other than the potato starch and the dehydroxanthan gum.

3. The cosmetic product according to claim 1, wherein the quantity of water is from 30 to 95% w/w relative to the total weight of the product.

4. The cosmetic product according to claim 1, wherein the quantity of potato starch is from 1 to 3% w/w relative to the total weight of the product.

5. The cosmetic product according to claim 1, wherein the potato starch is partially or completely modified.

6. The cosmetic product according to claim 1, wherein the quantity of dehydroxanthan gum is from 1 to 2% w/w relative to the total weight of the product.

7. The cosmetic product according to claim 1, wherein:
   the quantity of water is from 30 to 95% w/w relative to the total weight of the product;
   the quantity of potato starch is from 1 to 3% w/w relative to the total weight of the product; and
   the quantity of dehydroxanthan gum is from 1 to 2% w/w relative to the total weight of the product.

8. The cosmetic product according to claim 1, wherein the cosmetic product is provided in the form of hair gel.

9. A method for the temporary reshaping of keratinous fibers, wherein the method comprises the step of applying the cosmetic product according to claim 1 to the keratinous fibers.

10. The method of claim 9, wherein the cosmetic product is provided in the form of hair gel.

* * * * *